US012573472B2

(12) United States Patent
Hernandez et al.

(10) Patent No.: US 12,573,472 B2
(45) Date of Patent: Mar. 10, 2026

---

(54) METHODS FOR DETECTING VARIANTS IN NEXT- GENERATION SEQUENCING GENOMIC DATA

(71) Applicant: SOPHIA GENETICS SA, Saint-Sulpice (CH)

(72) Inventors: David Hernandez, Saint-Sulpice (CH); M. Zhenyu Xu, Saint-Sulpice (CH)

(73) Assignee: Sophia Genetics S.A., Rolle (CH)

( * ) Notice: Subject to any disclaimer, the term of this patent is extended or adjusted under 35 U.S.C. 154(b) by 1034 days.

(21) Appl. No.: 16/771,880

(22) PCT Filed: Dec. 12, 2018

(86) PCT No.: PCT/EP2018/084649
§ 371 (c)(1),
(2) Date: Jun. 11, 2020

(87) PCT Pub. No.: WO2019/115657
PCT Pub. Date: Jun. 20, 2019

(65) Prior Publication Data
US 2021/0074379 A1 Mar. 11, 2021

(30) Foreign Application Priority Data
Dec. 12, 2017 (EP) ..................................... 17206590

(51) Int. Cl.
*G16B 20/20* (2019.01)
*C12Q 1/6869* (2018.01)
*G16B 30/00* (2019.01)

(52) U.S. Cl.
CPC ........... *G16B 20/20* (2019.02); *C12Q 1/6869* (2013.01); *G16B 30/00* (2019.02)

(58) Field of Classification Search
None
See application file for complete search history.

(56) References Cited

PUBLICATIONS

Vis, J. K., Vermaat, M., Taschner, P. E., Kok, J. N., & Laros, J. F. (2015). An efficient algorithm for the extraction of HGVS variant descriptions from sequences. Bioinformatics, 31(23), 3751-3757. (Year: 2015).*
Johnson, T., Liebner, D., & Chen, J. L. (2017). Opportunities for patient matching algorithms to improve patient care in oncology. JCO Clinical Cancer Informatics, 1. (Year: 2017).*

(Continued)

*Primary Examiner* — Karlheinz R. Skowronek
*Assistant Examiner* — Mary C Leverett
(74) *Attorney, Agent, or Firm* — Bochner PLLC; Andrew D. Bochner; Caitlin A. Hyland

(57) ABSTRACT

A genomic data analyzer workflow may be configured to identify, with a variant annotation module, subsets of patient variants which match at least one medical reference variant database entry, even if the variant calling information in genomic data analyzer workflow and the database use different variant representations of SNP, MNP, INDELS and DELINS. In particular, database variants which are included into a subset of patient variants may be identified even if they do not exactly match the corresponding strings. The variant annotation module may be adapted to apply a branch-and-bound-like algorithm to efficiently process all possible subsets of patient variants in a genomic region.

17 Claims, 9 Drawing Sheets

(56) References Cited

PUBLICATIONS

Philippakis, A. A., Azzariti, D. R., Beltran, S., Brookes, A. J., Brownstein, C. A., Brudno, M., . . . & Rehm, H. L. (2015). The Matchmaker Exchange: a platform for rare disease gene discovery. Human mutation, 36(10), 915-921. (Year: 2015).*

Vandeweyer, G., Van Laer, L., Loeys, B., Van den Bulcke, T., & Kooy, R. F. (2014). VariantDB: a flexible annotation and filtering portal for next generation sequencing data. Genome medicine, 6, 1-10. (Year: 2014).*

Samwald, M., Minarro Gimenez, J. A., Boyce, R. D., Freimuth, R. R., Adlassnig, K. P., & Dumontier, M. (2015). Pharmacogenomic knowledge representation, reasoning and genome-based clinical decision support based on OWL 2 DL ontologies. BMC medical informatics and decision making, 15(1), 1-10. (Year: 2015).*

Tan, A., Abecasis, G. R., & Kang, H. M. (2015). Unified representation of genetic variants. Bioinformatics, 31(13), 2202-2204. (Year: 2015).*

Pabinger, Stephan, et al. "A survey of tools for variant analysis of next-generation genome sequencing data." Briefings in bioinformatics 15.2 (2014): 256-278. (Year: 2014).*

"A global reference for human genetic variation", Nature vol. 526 (7571), doi:10.1038/nature15393, The 1000 Genomes Project Consortium, Oct. 1, 2015, pp. 68-74.

" The Variant Call Format (VCF) Version 4.2 Specification", Jun. 25, 2020, Sequence Variant Nomenclature, available at https://github.com/samtools/hts-specs.

Garrison et al., "Haplotype-based variant detection from short-read sequencing", arXiv:1207.3907v2 [q-bi.GN], Jul. 20, 2012, http://arxiv.org/abs/1207.3907.

Erick Garrison, vcflib, "A C++ library for parsing and manipulating VCF files", "vcfallelicprimitives", "GitHub—Veflib", https://github.com/vcflib/vcflib, May 5, 2017.

Arash Bayat et al., "Improved VCF normalization for accurate VCF comparison", Bioinformatics, 33(7), pp. 964-970, Advance Access Publication Date: Dec. 30, 2016, XP055493329A.

John G. Cleary et al., "Comparing Variant Call Files for Performance Benchmarking of Next-Generation Sequencing Variant Calling Pipelines", First posted online Aug. 2, 2015, AuhXP055493311, Retrieved from the Internet: URL:http://dx.doi.0rg/1 0.1101/023754.full.pdf.

Extended European Search Report, mailed Aug. 3, 2018 by the European Patent Office (EPO), in European Application No. 17206590.6.

* cited by examiner

```
                                    1       10 14
                                    |        | |
Reference sequence:       tattccgatcttag Patient variants:         5: >CCGATGG
                          11:T>G Database  entry:          10:CT>GGCCGATC
                          G
```

```
                    1      10      20
                    |       |       |
```
a)   Reference sequence:   tattccgatcttagtcaaccag
b)   12:T>A
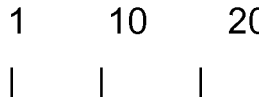
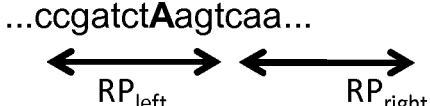
c)   5: >CCGATGG
d)   10:CTTA>
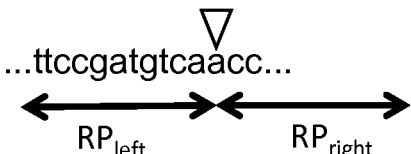
FIG. 5

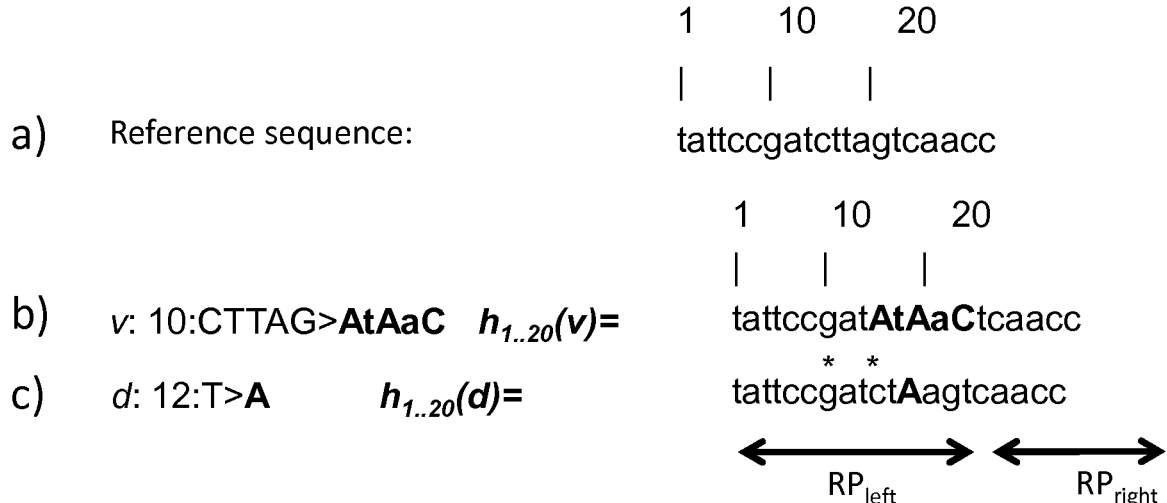
a)　　Reference sequence:
b)　　*v*: 10:CTTAG>AtAaC　　$h_{1..20}(v)=$
c)　　*d*: 12:T>A　　　　$h_{1..20}(d)=$
FIG. 6.1 a)    Reference sequence:
$$\begin{array}{ccc} 1 & 10 & 20 \\ | & | & | \end{array}$$
gtcttctcccaggtccaggc
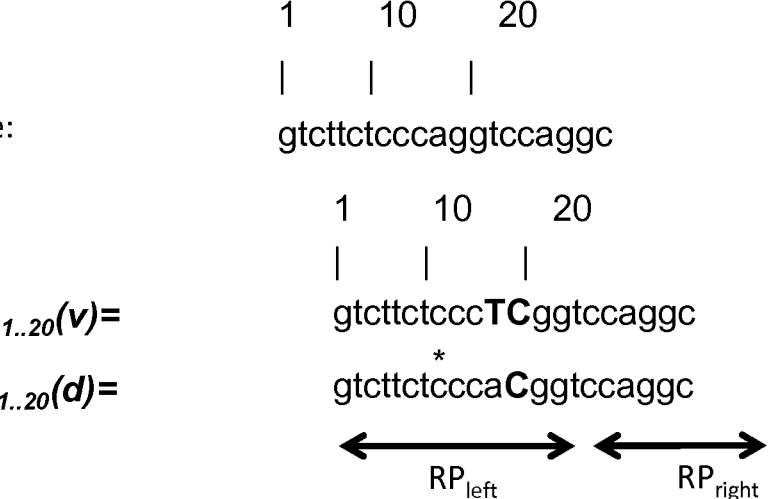
b)    v: 11:A>TC        $h_{1..20}(v)=$
$$\begin{array}{ccc} 1 & 10 & 20 \\ | & | & | \end{array}$$
gtcttctcccTCggtccaggc
c)    d: 12:  >C        $h_{1..20}(d)=$
gtcttctcccaCggtccaggc
$RP_{left}$        $RP_{right}$
FIG. 6.2 a) Reference sequence:
```
1       10      20      30
|       |       |       |
ctcccaggtccaggccattcttgaaccagg
```
b)   $d$ = 16:cattc>Ga
X = { 14:gcc>TcG , 20:ctt>   }
c)
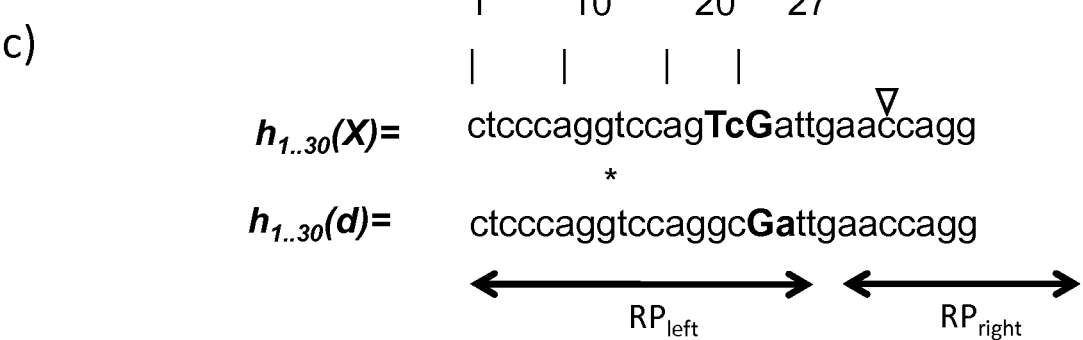
FIG. 6.3

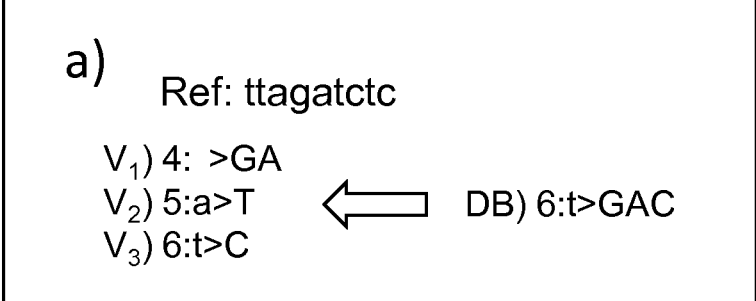
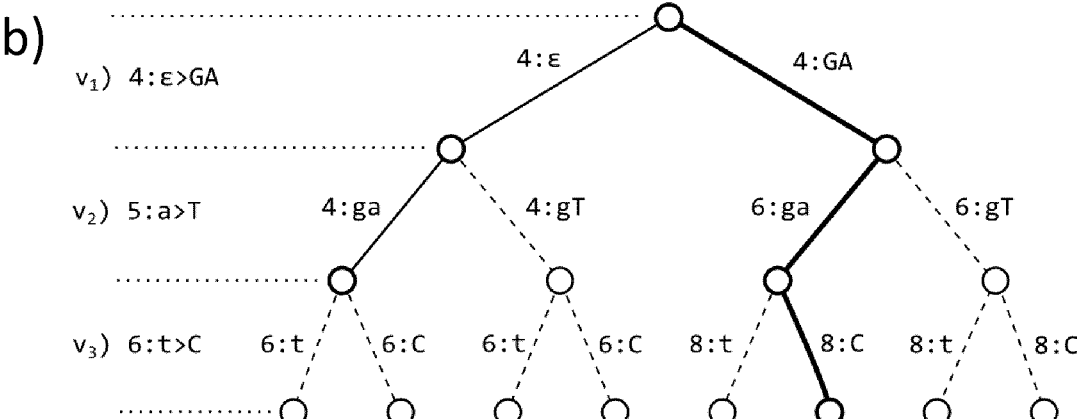
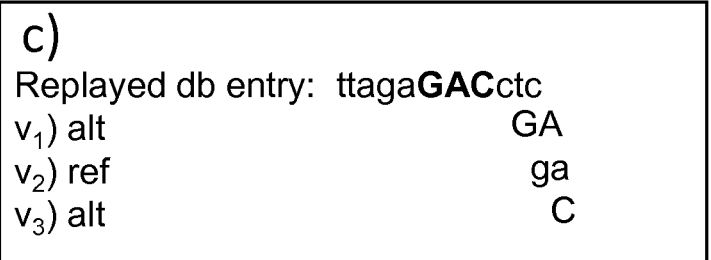
FIG. 7

METHODS FOR DETECTING VARIANTS IN NEXT- GENERATION SEQUENCING GENOMIC DATA

FIELD OF THE INVENTION

Methods described herein relate to genomic analysis in general, and more specifically to next generation sequencing applications.

BACKGROUND OF THE INVENTION

Next-Generation Sequencing

High throughput next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals (germline) or of cancerous tissues (somatic) can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference. An example of a commonly used reference is the human reference genome from the 1000 Genomes Project, Consortium 2015, as described in "A Global Reference for Human Genetic Variation." Nature 526 (7571): 68-74. doi:10.1038/nature15393, but other references may also be used as the human genome knowledge progresses.

Targeted Enrichment

In some pathologies, a specific gene variant has been associated with the illness, such as the BRCA1 and BRCA2 genes in certain forms of hereditary breast and ovarian cancers or the CFTR gene in cystic fibrosis. Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR™ or the Illumina TruSeq® Amplicon assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent SureSelect™ Target Enrichment System, Roche NimbleGen SeqCap EZ, Illumina Nextera Rapid Capture, Agilent Haloplex™ and Multiplicom MASTR™. In order to maximize the use of the massively-parallel processing NGS sequencer, a number of samples are multiplexed in the targeted NGS experiment—a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

Next Generation Sequencing Workflow Automation

In general, NGS raises specific data processing challenges as the reads are short and fragmented, thus making the mapping process to the reference genome chromosome alleles inherently ambiguous. The amount of data reads to be processed, combined with the multiple mapping solutions to be explored, requires significant computational resources. To bring the NGS genomic analyses to the level of sensitivity and specificity of the prior art biological analysis methods, dedicated statistical processing and artificial intelligence algorithms have to be developed by bio-informaticians to facilitate the interpretation of inherently noisy and ambiguous NGS data reads.

Next Generation Sequencing (NGS) enables in particular to detect and report small changes in the DNA sequence, such as single nucleotide polymorphisms (SNPs), multiple nucleotide polymorphisms (HNPs), insertions or deletions (INDELs), combinations of deletion(s) and SNP(s) (DELINS), as compared to the reference genome, through bioinformatics methods such as sequencing read alignment, variant calling, and variant annotation.

NGS workflows refer to the configuration and combination of such methods into an end-to-end genomic analysis application. In genomic research practice, NGS workflows are often manually setup and optimized using for instance dedicated scripts on a UNIX operating system, dedicated platforms including a graphical pipeline representation such as the Galaxy project, and/or a combination thereof. As clinical practice develops, NGS workflows may no longer be experimentally setup on a case-per-case basis, but rather integrated in SaaS (Software as a Service), PaaS (Platform as a Service) or IaaS (Infrastructure as a Service) offerings by third party providers. In that context, further automation of the NGS workflows is key to facilitate the routine integration of those services into the clinical practice.

Next Generation Sequencing Variant Calling Data

Sequence variations, simply called variants, can be described in the NGS workflow by a compact string representation that specifies the local biological sequence mutations. They are not only limited to genomic sequence but can also be used to describe mutations occurring on other biological sequence types such as the translated protein sequence. A standardized variant nomenclature is defined in the Human Genome Variation Society (HGVS) web site ("Sequence Variant Nomenclature" 2017). Variants at the genomic level are generally stored in the variant call file (VCF) text format, but alternative formats may also be used. A convenient human readable format is the x:ref>alt variant notation, where x specifies the coordinate of the variant in the reference sequence, ref is allele string from the reference, and alt is alternate allele string from the patient. For example, 3:A>T means that the 'A' in position 3 is changed to a 'T'. 11:C>CTTAC means that the string "TTAC" is inserted just after the symbol "C" at position 11. Insertion and deletion (indel) variants are commonly specified by including the symbol that precedes the indel site. This preceding position is referred to as the anchor. However, the anchor is not necessary to specify the variant. The insertion 11:C>CTTAC could be equivalently noted by the NGS workflow as 12: ε>TTAC, which means that the sample displays a "TTAC" insertion just before the $12^{th}$ symbol in the reference, where the symbol 'ε' denotes an empty reference allele.

Once a list of variants has been obtained for a given sample, a crucial step for the characterization and annotation of those variants is to retrieve relevant entries from public or private variants databases, which provides inestimable information for diagnosis and personalized medicine treatment, such as the variants frequency in the population, their pathogenicity, clinical trials annotations, cancers drug response, etc. This collected information them contribute in turning the patient data into actionable clinical insights.

In practice, retrieving relevant variants from reference databases involves a matching or comparison procedure between the analyzed patient variants and the reference ones that are stored in the databases. Matching variant calling data information is however not trivial because of their nature: they are not uniquely defined entities but rather correspond to sequence differences as determined by a certain sequence alignment model. While the real sequence is uniquely defined for both the patient and the reference sequence, the observed variations when comparing them may vary according to the NGS workflow and parameters of the genomic analyzer system the patient sample was submitted to. First, the read alignment module of the genomic analyzer system may align the sequence onto the reference differently, depending on the alignment model and parameters they use. Second, the variant calling module may be parameterized to output variants only into their canonical form (i.e SNP, deletion and insertion only), or to assemble the variants into longer haplotypes, resulting in non-canonical complex variants such as MNPs or DELINS. Thus, a proper comparison procedure is needed to ensure that the reported database entries from the variant calling module in any genome analyzer workflow depend on the actually analyzed data, and not on the particular workflow that was used to analyze this data.

Here is a simple example that illustrates such different representations: let R be a reference sequence "TCAC" and P be a patient sequence as "TCTGC". Here are two ways to represent the difference between the patient and the reference sequence:

| Representation 1 | Representation 2 |
|---|---|
| v1) 3:A>T ('A' in position 3 is mutated to a 'T') | v12) 3:A>TG ('A' in position 3 is replaced by 'TG') |
| v2) 4:ε>G (= "G" insertion just before the position 4) | |

The first representation enumerates the sequence differences between R and P as two individual variants v1 and v2, while the second one involves a single variant v12. Those two representations are however strictly equivalent from a functional point of view.

A generic database search allows retrieving the variants using an exact comparison between the variant components (position coordinate pos, reference ref, alternative alt) in a variant calling file and the database index. Depending on the index, such retrieval is generally very efficient with a time complexity $O(\log 2(|D|))$ with $|D|$ being the number of entries in the database. However, such an approach is only able to retrieve entries that are identical to the searched feature and does not account for the fact that a mutation event in the sample could be represented differently in the database. Suppose for example that the v12 variant 3:A>TG is a database entry, and that two variants: 3:A>T and 4:ε>G were reported in the NGS workflow for a patient sample. A generic database search that only compares the coordinates, ref and alt strings will miss the match because the representations between the queried variants and the one in the database is not the same. As will be apparent to those skilled in the art of bioinformatics, generic database search functions can only identify variants that are identical to the queried one but would miss the matches that represent the same mutation differently. This example illustrates that a dedicated database retrieving approach is needed to identify all matches in a database, which is of primary importance in a clinical diagnostic context. Strategies to compare variants with different representations have already been proposed and are publicly available. However, none of them are currently applicable to variants database retrieval. They are rather developed for VCF files comparisons. Most of these prior art methods apply a variant normalization approach, wherein the variants to be compared are first normalized to a common standard. The underlying idea is that once both sets of variants have been converted to some standard, they can be straightforwardly compared using a generic matching procedure that only compares the coordinates and ref/alt strings. The simplest normalization procedure consists in discarding the contextual nucleotides and in shifting the indels to their left-most position, as described for instance by Tan et al. in "*Unified Representation of Genetic Variants*", Bioinformatics (Oxford, England) 31 (13): 2202-4. doi: 10.1093/bioinformatics/btv112 or by Talwalkar et al. in "*SMaSH: A Benchmarking Toolkit for Human Genome Variant Calling*" Bioinformatics (Oxford, England) 30 (19): 2787-95. doi: 10.1093/bioinformatics/btu345. The Useq VCF compactor open source software operates in the same way. These approaches however do not deal with the complex (i.e non-canonical) variants. One way to normalize complex variants is to decompose them into their canonical building blocks. This process is implemented in the "vcfallelicprimitives" software module, which is part of the vcflib open source software package, as published by Garrison et al. in "Haplotype-Based Variant Detection from Short Read Sequencing" arXiv: 1207.3907 [Q-Bio], July 2012. It is worth noting that this package also features the program "vcfgeno2haplo", which performs the reverse operation that consists in merging several variants into a larger complex variant. A further improved normalization method is described in Bayat et al. *"Improved VCF normalization for accurate VCF comparison", Bioinformatics,* 19 Dec. 2016, page btw7 48, XP05 5493329, GB ISSN: 1367:4803, DOI: 1093/*bioinformatics/btw*7 48, where all the variants in the variant calling file are applied to the reference genome to reconstruct a sample genome. After that, the variants need to be called once more by comparing this sample genome to the reference genome (best alignment normalization—BAN).

As will be apparent to those skilled in the art of bioinformatics, though providing some valuable improvements when compared to a naive matching procedure, normalizing the variants to some standard only allows addressing specific variant representation differences but does not provide a generalized and computationally efficient solution to the problem. Another method implemented in the "vcfeval" module as part of the freely available RTG Tools software package provides a more generic approach. Unlike previously described methods that work by normalizing variants into their simpler minimal form, they perform the opposite operation: they merge variants into larger haplotypes and compare those haplotypes directly. In *"Comparing Variant Call Files for Performance Benchmarking of Next-Generation Sequencing Variant Calling Pipelines,"* August 2015 ([Cleary2015]), Cleary et al. described the vcfeval algorithm as a dedicated method to compare two variants sets that were obtained from germline samples. Such a method may be used to assess the performance of variants detection pipelines by using a gold standard set obtained from a well characterized sample. This variant calling post-processing method compares C, a set of variants obtained from a given workflow, and B, a gold standard variants set for the analyzed sample. The method classifies each variant from C as TP (true positive), FP (false positive) and FN (false negative) in accordance with its matching status to the gold standard. The vcfeval software module allows matching variants between C and B whatever their representations. It optimizes the way of assembling variants into larger haplotypes regarding the maximization of the number of agreements between the two sets. In other words, the program searches for the haplotypes combination that maximizes the number of true positives. As will be apparent to those skilled in the art of bioinformatics, one problem however is the combinatorial nature of such a method when applied to a robust NGS genome analyzer SaaS or SaaP system operating with a diversity of patient sample sources with possibly different sequencing technologies, read alignments and variant calling modules parametrization over time. In a germline data experiment, the variants that are called may be issued from three components: there can belong to any one of the two complementary alleles, or from the noise (sequence errors or sequence alignment artifacts). There are thus $3^{|B|+|C|}$ possible combinations. The vcfeval program circumvents this problem with a dynamic programming approach to explore the possible variants combinations under a diploid context. Their algorithm guarantees to find the combination that maximizes the number of agreements between C and B. The dynamic programming algorithm performs the variant comparisons by elongating a possible haplotype in a stepwise way with a haplotype function h(V ,k) )→p that replays into the reference sequence R the first k variant from a subset V. As will apparent to those skilled in the art of bioinformatics, the [Cleary2015] method of replaying a set of variants consists in reconstructing the patient sequence string p from the variant string V and the reference sequence string R. The resulting reconstructed patient haplotype p may be represented as a string that concatenates in turn the variant string subsequences V from the variants, and the ones from the reference sequence R. By construction, P embeds all mutations in V as compared to R. Note that this process is equivalent to merging a set of variants into a single larger one as performed by "vcfgeno2haplo" from the vcflib package.

Merging variants by replaying them into larger haplotypes, as proposed in [Cleary2015] and implemented in the vcfeval program, allows assessing the equivalence of two sets of variants, as illustrated by the example of FIG. 1. As illustrated on FIG. 1a) two patient variants, an insertion of the CCGATGG string just before the position 5 and a SNP of the T nucleotide replaced by the G nucleotide at position 11 may be compared to a reference variant database entry of a DELINS wherein the CT polynucleotide string at position 10 is deleted and replaced with the GGCCGATCG string. As illustrated on FIG. 1b), the patient variants and the database entry may respectively be replayed into the reference sequence as disclosed for instance in [Cleary2015]. Synced and out of sync regions are depicted with the plain and dashed arrows respectively. As can be observed in FIG. 1b), the replayed haplotypes compare exactly and start and end at the same reference coordinates, which means that the two mutations representation are equivalent. As disclosed in [Cleary2015], this replay can be achieved by choosing two synchronization points that are external to the variants from both set, and by producing the haplotypes of both sets starting and ending at a synchronization start point s and end point e, such that the variants are enclosed between the start point s and the end point e. This approach guarantees that differently represented mutations are matched. However, given a set of variants obtained from a patient sample, there is an exponential number of ways to combine the individual variants into larger haplotypes. Such an approach requires thus to design a combinatorial heuristic to be computationally tractable.

This restricts the efficient deployment of NGS workflows, as there does not currently exist a method to identify variants matches in a database in a robust way (independently from the patient sample variant calling representations and from the reference variant database representations respectively), that can be automated in a cost-effective way. Existing NGS workflows were initially developed for academic research purposes by highly specialized personnel on a case-per-case basis to meet the clinical expectations in terms of specificity and sensitivity. The computational resources allocated to those workflows now have to scale up to meet the needs of large-scale routine genomic analysis for diagnosis and personalized medicine treatment purposes. The automation of genomic data processing workflows is particularly challenging as the existing bioinformatics methods developed for NGS research workflows have not been optimized for computational efficiency in large-scale deployments. There is therefore a need for a better solution to automatize the genomic data processing variant calling post-processing in NGS workflows for data-driven medical applications, so that the same genomic data processing platform may operate with reasonable computational resources on a diversity of genomic data as may be generated from different next-generation sequencing laboratory setups, while optimizing the detection of variants of medical relevance regardless of the diversity of the underlying variant calling data and variant reference databases representations without necessitating cumbersome manual processing of the genomic data by the end users.

BRIEF SUMMARY

The present disclosure addresses the above needs by proposing a method and a genomic data analyzer for identifying, with a variant annotation module on at least one data processor, if the variant calling information of a patient sample includes at least one variant entry in at least one medical variant reference database, a variant v being defined by a start coordinate s(v), an end coordinate e(v) and a string alt(v) of a genomic variation relative to a human genome reference string R, characterized in that the method comprises the steps of:

acquiring the variant calling information of the next generation sequencing data of a patient biological sample, the variant calling information comprising a set V* of genomic variants in at least one genomic region to be analyzed;

retrieving, in the at least one medical variant reference database, a subset $D=\{d_1, d_2, \ldots, d_{|D|}\}$ of reference variant entries that may be matched to at least one variant in the patient set of genomic variants V*;

selecting, for each variant database entry $d \in D$, a subset $V=\{v_1, v_2, \ldots, v_{|V|}\}, V \subseteq V^*$, of patient variants that may be matched to the variant database entry d;

selecting an extended genomic region coordinate range a . . . b so as to include the start and end coordinates from the database patient variants in the subset V, as well as the start and end coordinate of the variant database entry d;

reconstructing over the extended genomic region coordinate range a . . . b the database variant haplotype string $h_{a \ldots b}$ (d) for the reference variant entry d as the concatenation of three genomic information strings $RP_{left}$+alt(d)+$RP_{right}$, wherein alt(d) is the alternative string characterizing the variant d, $RP_{left}$ is a string corresponding to extended genomic region on the left of the variant alt(d) in the reference human genome R and $RP_{right}$ is a string corresponding to extended genomic region on the right of the variant alt(d) in the reference human genome R;

reconstructing over the extended genomic region coordinate range a . . . b the patient variant haplotype string $h_{a \ldots b}$ (X) , X being a subset of the selected region variant calling information V comprising at least one selected patient variant $v_j$;

identifying that the variant calling information of the patient sample includes the medical variant database entry d if the length of the reconstructed database variant haplotype string $h_{a \ldots b}$ (d) equals the length of the reconstructed patient variant haplotype string $h_{a \ldots b}$ (X), the reconstructed patient variant haplotype string $h_{a \ldots b}$ (X) differs from the reconstructed database variant haplotype string $h_{a \ldots b}$ (d) by at least one mismatch in either the $RP_{left}$ string or the $RP_{right}$ string of the reconstructed database variant haplotype string $h_{a \ldots b}$ (d), and every variants in the subset X of patient sample variants overlap by at least one symbol the location defined by the start and the end coordinates of the database variant entry d.

In a possible embodiment, the extended region string $RP_{left}$ on the left of the variant alt(d) is an empty string and the extended region string $RP_{right}$ on the right of the variant alt(d) is at least one symbol long.

In another embodiment, the extended region string $RP_{right}$ on the right of the variant alt(d) is an empty string and the extended region string $RP_{left}$ on the left of the variant alt(d) is at least one symbol long.

According to one embodiment, the horizon parameter z is calculated as a function of the maximum distance an INDEL could be shifted into an alternate equivalent alignment, of the maximum length of the genomic variants, of the read length, or of a combination thereof. It can be further predefined as a length of 500 symbols, 100 symbols, 200 symbols, 300 symbols, 400 symbols, 600 symbols, 700 symbols, 800 symbols, 900 symbols, 1000 symbols, or 1500 symbols

BRIEF DESCRIPTION OF THE DRAWINGS

FIG. 5 shows exemplary left and right reference context region substrings $RP_{left}$ and $RP_{right}$ respectively for three variant examples: a) a SNP, b) an insertion and c) a deletion.

FIG. 6.1 shows an example of an included match between an MNP patient variant and a simple SNP medical variant reference database entry.

FIG. 6.2 shows an example of an included match between a DELINS and an insertion.

FIG. 6.3 shows an example of an included match between a database DELINS, and a patient set of two variants, comprising a MNP and a deletion.

FIG. 7 illustrates an example of a possible branch-and-bound-like combinatorial optimization algorithm that efficiently explores possible ways to combine the patient variants to identify any variant or combinations or variants that directly or indirectly match a medical reference variant database entry.

DETAILED DESCRIPTION

Next Generation Sequencing Analysis System

Figure 1:
FIG. 1a) illustrates an example of different variant representations for the NGS variant calling information of a patient sample and a reference database entry, while FIG. 1b) illustrates they can be found equivalent by reconstructing the corresponding sequence strings that embed the mutations.
Figure 2:
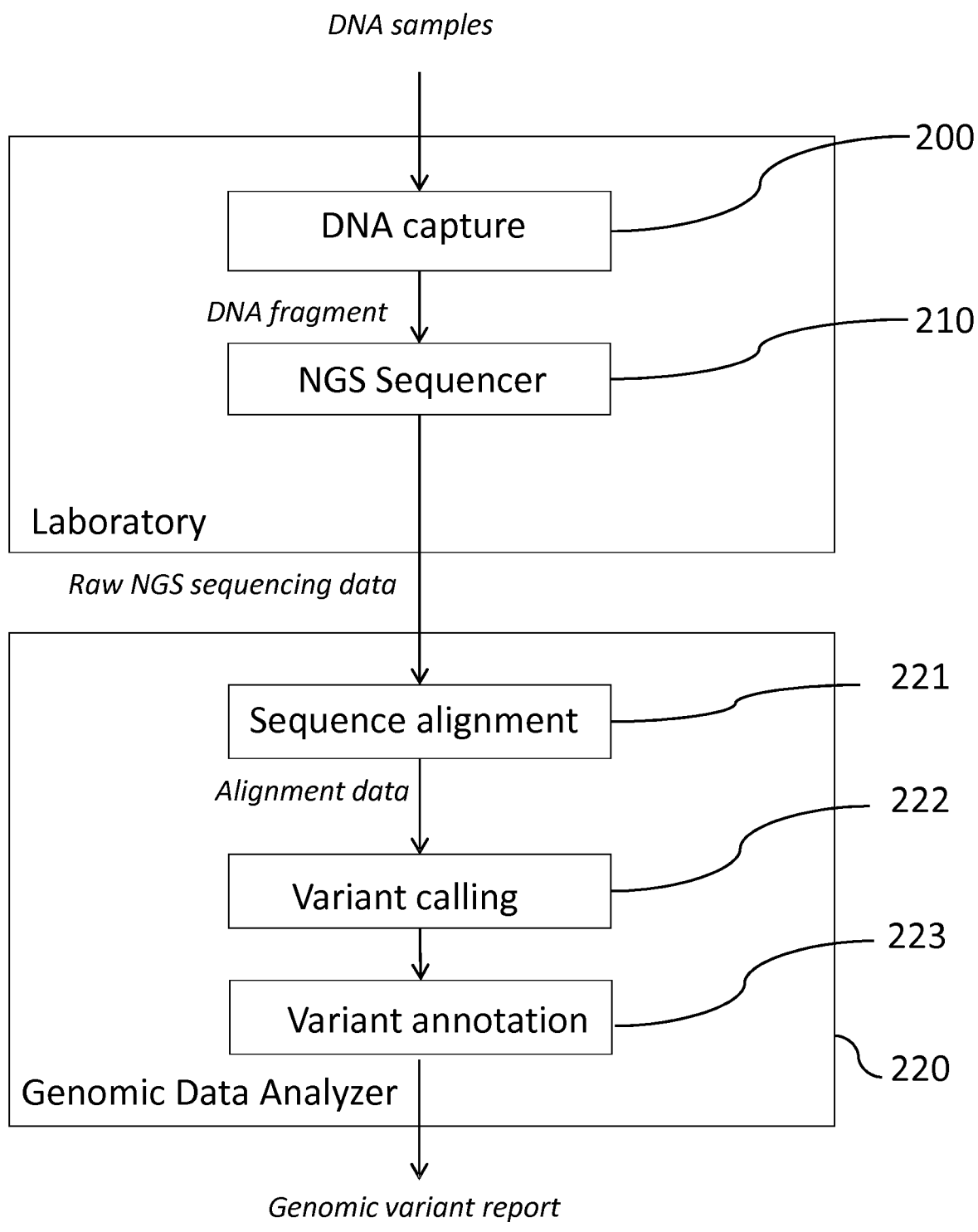
FIG. 2 represents an exemplary next generation sequencing system.

FIG. 2 shows an exemplary genomic analysis system comprising a DNA enrichment assay 200, a next generation sequencer 210 and a genomic data analyzer 220.

In an NGS laboratory, a pool of DNA samples is processed by the DNA enrichment assay 200 to generate a library of pooled amplicons (for amplicon-based enrichment) or fragments (for probe-based enrichment) as DNA fragments input to the next generation sequencer 210, each set of amplicons/fragments corresponding to a different sample. The number of amplicons/fragments is application dependent. In some genomic analysis experiments, target enrichment may require 150 primers to enrich 75 different regions to be targeted out of the sample genome, resulting in a set of 75 amplicons for each sample. The number of samples may also be adapted to the next-generation sequencing sequencer 210 parallel processing capability, for instance 48 samples in the form of a library of pooled amplicons may be sequenced in parallel by an Illumina MiSeq sequencer. Other NGS sequencer technologies may be used, such as for instance the Roche 454™ GS Junior or GS FLX, Illumina MiSeq®, or Life Technologies Ion PGM™ sequencers.

The next-generation sequencer 210 analyses the input samples and generates sequence reads in a computer-readable file format representing raw NGS sequencing data. Depending on the NGS technology, one or more files may be output by the NGS sequencer 210. In some embodiments, for instance with Illumina sequencers, the FASTQ file format may be used with two different files for forward and reverse reads or as a single joined file. This text file typically starts with a sequence header marked by a '@' start character, followed by one line of sequence information represented as a string of 'A', 'T', 'C', 'G' nucleotide characters, then by a quality header marked by a '+' start character, followed by one line of quality metrics, one quality score matching each nucleotide read. The format for the quality metrics for each nucleotide in the sequence information string may depend on the sequencer. Some legacy sequencers output the raw sequencing data in the SFF (Standard Flowgram Format) binary file format, which comprises an informative header and the read data. Other embodiments are also possible, for instance some legacy Roche sequencers output multiple FASTQ files for a single patient analysis, while other sequencers, for instance the Ion Torrent PGM sequencers, have migrated to the compressed unmapped BAM file format, as may be recognized from the .basecaller.bam file extension. As known to those skilled in the art of communication systems, the laboratory operates a computing infrastructure to store the resulting raw NGS sequencing data file in a laboratory biobank. The laboratory computing infrastructure connects, with authentication credentials, through a communication network, to the genomic data analyzer 220 and transmits a genomic analysis request comprising the raw NGS sequencing file to the genomic data analyzer 220.

The genomic data analyzer computer system (also "system" herein) 220 is programmed or otherwise configured to implement different genomic data analysis methods, such as receiving and/or combining sequencing data and/or annotating sequencing data.

The genomic data analyzer 220 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. Examples of genomic data analyzer computing systems, environments, and/or configurations include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and the like. In some embodiments, the computer system may comprise one or more computer servers, which are operational with numerous other general purpose or special purpose computing systems and may enable distributed computing, such as cloud computing, for instance in a genomic data farm. In some embodiments, the genomic data analyzer 220 may be integrated into a massively parallel system. In some embodiments, the genomic data analyzer 220 may be directly integrated into a next generation sequencing system.

The genomic data analyzer 220 computer system may be adapted in the general context of computer system-executable instructions, such as program modules, being executed by a computer system. Generally, program modules may include routines, programs, objects, components, logic, data structures, and so on that perform particular tasks or implement particular abstract data types. As is well known to those skilled in the art of computer programming, program modules may use native operating system and/or file system functions, standalone applications; browser or application plugins, applets, etc.; commercial or open source libraries and/or library tools as may be programmed in Python, Biopython, C/C++, or other programming languages; custom scripts, such as Perl or Bioperl scripts.

Instructions may be executed in distributed cloud computing environments where tasks are performed by remote processing devices that are linked through a communications network. In a distributed cloud-computing environment, program modules may be located in both local and remote computer system storage media including memory storage devices.

As illustrated on FIG. 2, the genomic data analyzer 220 may comprise a sequence alignment module 221, which compares the raw NGS sequencing data to a reference genome. The sequence alignment module 221 may be configured to execute different alignment algorithms. Standard raw data alignment algorithms such as Bowtie2 or BWA that have been optimized for fast processing of numerous genomic data sequencing reads may be used, but other embodiments are also possible. The alignment results may be represented as one or several files in BAM or SAM format, as known to those skilled in the bioinformatics art, but other formats may also be used, for instance compressed formats or formats optimized for order-preserving encryption, depending on the genomic data analyzer 220 requirements for storage optimization and/or genomic data privacy enforcement.

The resulting alignment data may be further filtered and analyzed by a variant calling module 222 to retrieve variant information such as SNP, MNPs, INDELs and DELINS polymorphisms. The variant calling module 222 may be configured to execute different variant calling algorithms to output the information into a variant calling file in the VCF file format, but other formats may be used too.

As illustrated on FIG. 2, the variant calling information may then be processed by a variant annotation module 223 which may be configured to analyze the variant calling information, to match it against medical reference variant databases information, and to generate a genomic variant report synthesis which further facilitates the diagnosis and the personalized medicine treatment for the analyzed patient.

The variant annotation module 223 of the genomic data analyzer 220 may thus be adapted to automatically identify in the variant calling information, with a processor, a set of variants which have been listed in one or more reference variant database storage. It is to be noted that the expression "database variants" can be understood as representing all variants stored in a storage device or a group of variants stored in a storage device and organized as a group. The variant annotation module 223 may be adapted to query entries into the reference database, with a processor. In a possible embodiment, the variant annotation module 223 sends queries and receives answers from a remote medical reference variant database storage through a communication network such as the internet. An example of such a medical reference variant database storage is Clinvar (https://www.ncbi.nlm.nih.gov/clinvar/) but other online variant databases may also be used, as will be apparent to those skilled in the art of clinical bioinformatics. In an alternative embodiment, the genomic data analyzer may send queries and receive answers from a local memory storage replicate of a medical reference variants database.

The variant annotation module 223 may be fully integrated as part of the software workflow of an end-to-end genomic data analyzer 220 or it may operate as a stand-alone module which processes upon request an input variant calling data file of a patient sample in any variant data analyzer workflow (not represented) to annotate variants of possible clinical relevance. In a possible embodiment, the variant annotation module 223 may be integrated in a client-server architecture, but other embodiments are also possible.

The proposed variant annotation module 223 may identify variants from a specific version of a medical reference variant database such as for instance Clinvar or COSMIC. In a possible embodiment, a diversity of medical reference variant databases may be parsed and compiled into a single merged reference database prior to running the genomic analysis workflow on a diversity of patient sample analysis requests. In an alternate embodiment, the proposed variant annotation module 223 may also independently refer to various medical reference variant databases in search for all possible references, either sequentially with at least one processor or in parallel with different processors. The proposed variant annotation module 223 may associate the version and reference of the medical reference variant database with the identified patient variants to annotate 346 the patient variants by retrieving the variant attributes in this database version, and may report 350 this reference information to the end user together with the retrieved variants and their attributes. When the same variant is detected 345 in different databases, the proposed variant annotation module 223 may only keep one occurrence to avoid redundant variant annotation 346. In a possible embodiment, only the attributes from the most recent database version are retrieved. In another possible embodiment, the proposed variant annotation module 223 may annotate the variant by merging attributes retrieved from different reference databases, to avoid redundant reporting 350 to the end user while reporting as many attributes as could be retrieved for any identified variant. Other embodiments are also possible.

The proposed variant annotation module 223 may thus serve next generation sequencing genomic analysis requests from different labs that are independently operating different sequencer technologies and different DNA enrichment technologies on different samples for different genes, by comparing the variant calling information from each sample patient NGS analysis to one or more medical reference variant databases. The proposed variant annotation module 223 may automatically and efficiently detect which entries in at least one reference variant database do match the sample variant calling information out of the variant calling module 222, even if the patient variant calling information and the reference variant database use different variant data representation encoding models.

Figure 3:
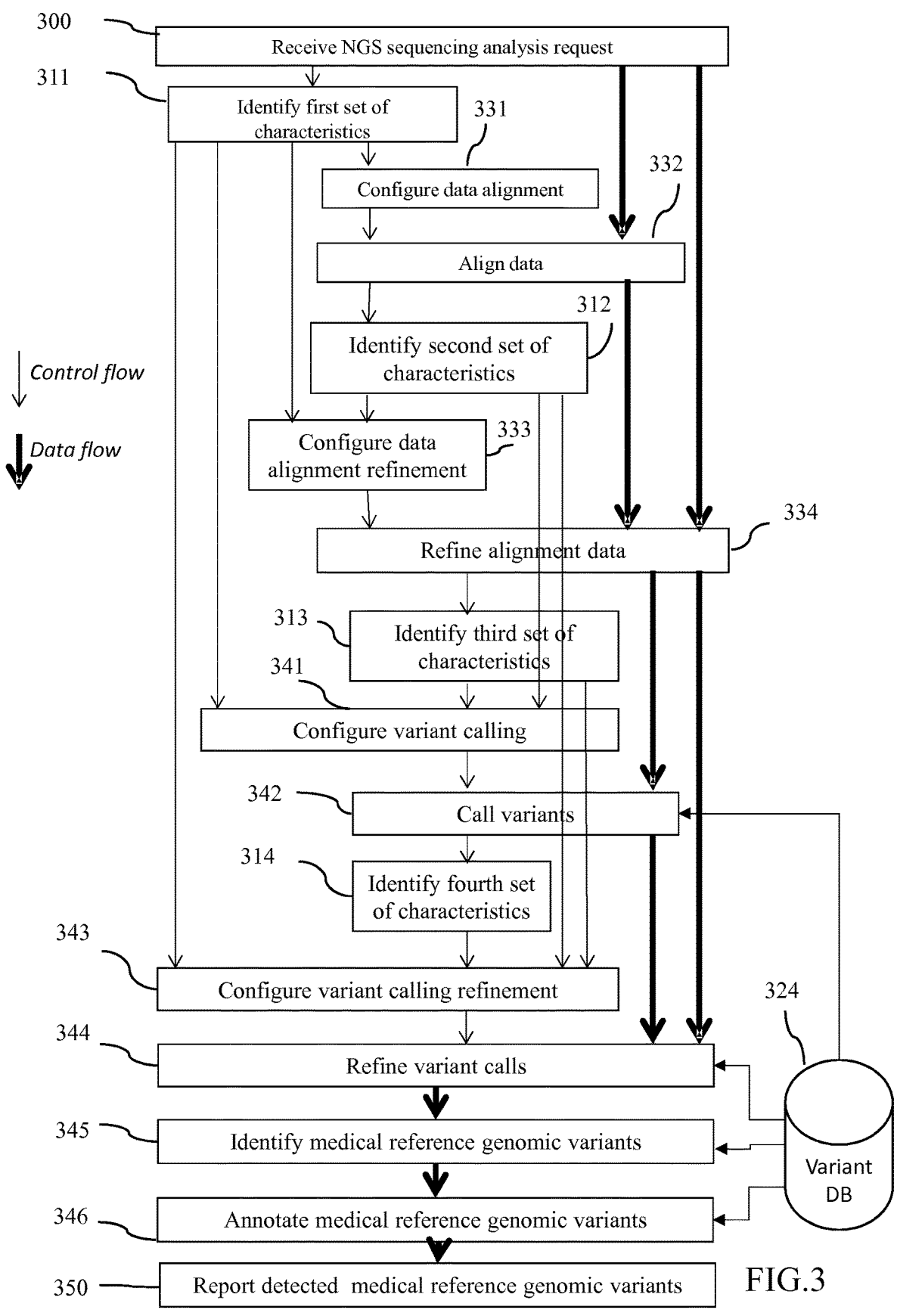
FIG. 3 shows the flowchart of a next generation sequencing genomic analysis workflow.

FIG. 3 shows accordingly an exemplary end-to-end genomic analysis workflow for the genomic data analyzer 220, comprising:

receiving 300 a next generation sequencing analysis request;

identifying 311 a first set of characteristics associated with the next generation sequencing analysis request, the first set of characteristics comprising at least a target enrichment technology identifier, a sequencing technology identifier, and a genomic context identifier;

configuring 331 a data alignment module 221 to align the input sequencing data in accordance with at least one characteristic of the first set of characteristics;

aligning 332, with the configured data alignment module 221, the input sequencing data to a genomic sequence, and reporting the alignment data into a raw alignment data file;

identifying 312 a second set of characteristics associated with the alignment data from the raw alignment data file, the second set of characteristics comprising at least a data alignment pattern identifier;

configuring 333 the data alignment module 221 to refine at least one subset of the input sequencing data in accordance with at least one characteristic of the first set of characteristics and at least one characteristic of the second set of characteristics;

refining 334, with the configured data alignment module 221, the subset of the input sequencing data to produce a refined alignment data file;

identifying 313 a third set of characteristics associated with the re-alignment data from the refined alignment data file, the third set of characteristics comprising at least a genomic context identifier;

configuring 341 a variant calling module 222 to detect variants associated with the refined alignment data in accordance with at least one characteristic of the first set of characteristics, at least one characteristic of the second set of characteristics, and at least one characteristic of the third set of characteristics;

detecting 342 a first set of genomic variants, with the configured variant calling module 222, in the refined alignment data;

identifying 314 a fourth set of characteristics associated with the detected genomic variants, the fourth set of characteristics comprising at least a variant calling refinement identifier;

configuring 343 the variant calling module 222 to detect variants associated with the refined alignment data in accordance with at least one characteristic of the first set of characteristics, at least one characteristic of the second set of characteristics, at least one characteristic of the third set of characteristics and at least one characteristic of the fourth set of characteristics;

detecting 344 refined genomic variants, with the configured variant calling module 322, in the refined alignment data and the detected genomic variants, to produce a refined variant calling information data set of genomic variants;

identifying 345 medical reference genomic variants, with the configured variant annotation module 323, in the variant calling information data, each medical reference genomic variant being listed as one entry into at least one medical reference variant database 324;

annotating 346 the medical reference genomic variants, with the configured variant annotation module 323, according to the matching medical reference variant database 324 entries;

reporting 350 the annotated genomic variants.

Exemplary Embodiments

An exemplary embodiment of a proposed referenced genomic variant identification method 345 will now be described in more detail. The fully automated variant annotation module 223 in the genomic data analysis workflow of FIG. 2 operates on variant calling data information sourced from at least one patient sample with reference to at least one variant reference database.

First, we observed that contrarily to variants that are issued from the same sample, medical reference database variants are generally independent from each other. In most cases, they were obtained at a different time, from a diversity of samples, from different tissues, under different conditions, and by different laboratories. This is a significant difference as compared to the genomic variants of a single patient sample, where all variants were obtained during a single experiment from the same sample with a single bioinformatics workflow. Such patient variants may be interdependent because they were all determined from a single alignment of the patient sequence onto the same version of the human reference genome. Some patient variants can thus be combined into other equivalent representations.

On the contrary, since medical reference database variants are independent, they cannot be combined into a larger valid haplotype. Therefore, a medical reference genomic variant match always involves a single database entry. However, the patient variants that are matched could be multiple. This statement has an important implication on the combinatorial nature of the problem: while there are multiple combinations of the patient variants to be assessed, there is a single possible haplotype for the database entry; this means that the database haplotype may be fixed during the optimization process of the referenced entries identification 345. The variant annotation module 223 may thus be adapted to exploit this constraint in the combinatorial search approach for better computational efficiency.

Figure 4:
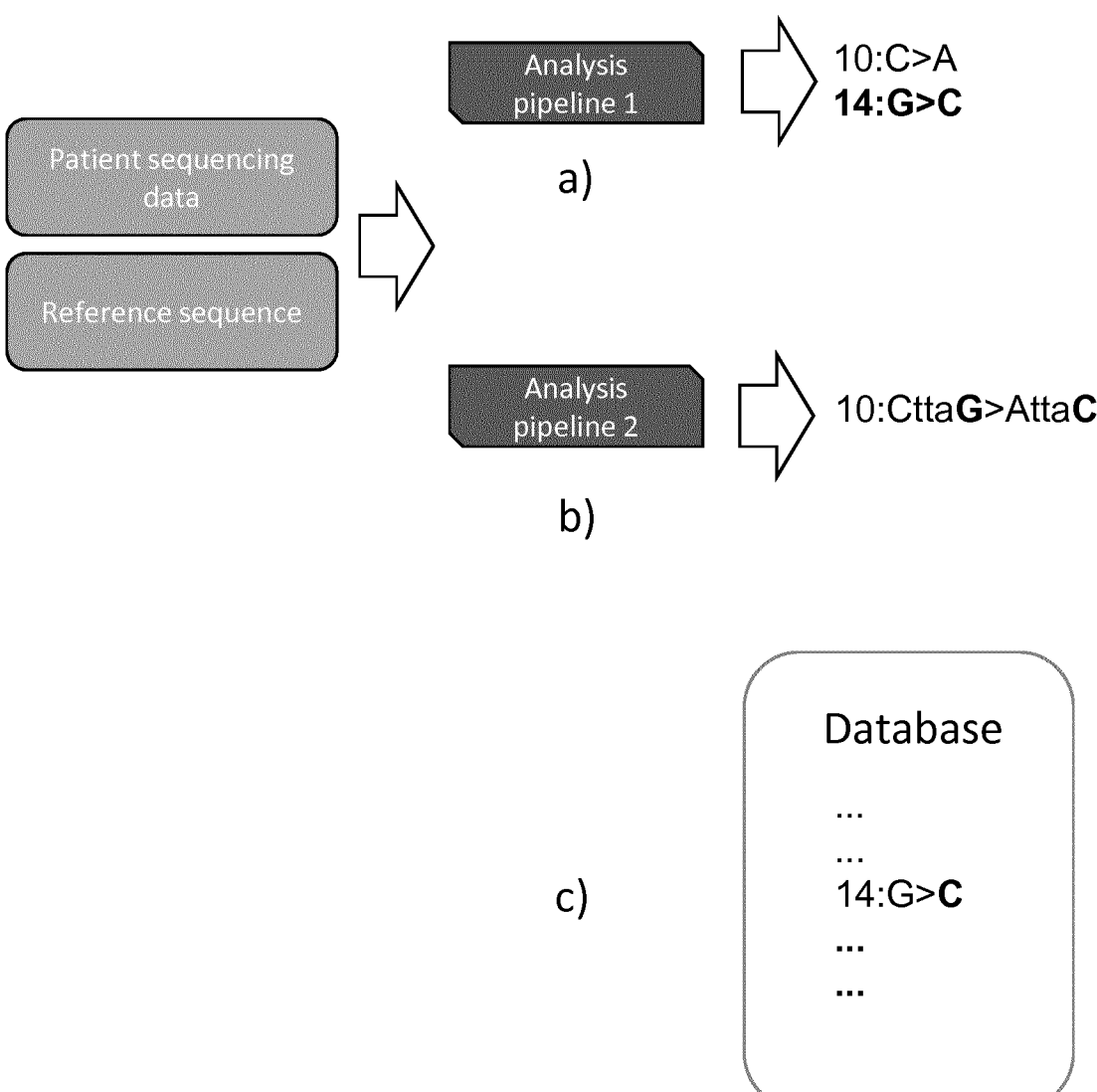
FIG. 4 illustrates the need for a more robust database matching method with an example wherein different prior art NGS genomic analysis workflow may produce different representations of the same patient sample functional variant according to their pipeline algorithms.

We also observed that the existing variants matching algorithms only focus on identifying exact matches. When comparing the variants from two samples, an exact match between two variants or a set of variants implies that the two representations are strictly equivalent. In [Cleary2015], the variants that are not involved in exact matches between the analyzed pipeline and the reference standard are either classified as false positive FP or as false negative FN depending on whether they belong to the querying or to the queried set. However, this FP and FN classification and overall the minimization of their occurrences while maximizing the number of true positive exact match hits (TP) are only suited in the context of comparing two variant sets that were obtained from the same sample, but using different sequencing technologies and/or different bioinformatics analysis pipelines. This classification does not apply in our independent, non-standardized database search context. Indeed, certain non-exact matches with the reference database entries still need to be considered in the identification 345 of medical reference genomic variants out of variant calling information, as illustrated by the example of FIG. 4. An exemplary patient sample variant may be represented as two individual SNPs 10:C>A and 14:G>C variants when analyzed in a first genomic analyzer workflow 1 (FIG. 4*a*) while it may be represented as a single complex non-canonical MNP variant 10:CttaG>AttaC MNP while analyzed in a second workflow 2 (FIG. 4*b*). If the medical reference database entry comprises the second individual SNP 14:G>C (FIG. 4*c*), only the first workflow will identify 345 the exact match, but the second workflow should also identify 345 a medical reference database variant match 14:G>C because this entry is an individual component of the MNP. Therefore, such included matches need to be identified 345, annotated 346 and reported 350 as well as the exact matches by the proposed improved variant annotation module 223.

Let $R=\{r_1, r_2, \ldots, r_m\}$ denote a reference sequence string of length m where $r_i$ is the $i^{th}$ symbol in the R string. $R_{i \ldots j}$ denotes the substring of R that starts and ends at position i and j respectively. R can be a sequence of any type such as a human chromosome sequence or a region only, such as a gene, an exon, a cDNA sequence or protein sequence. A patient variant on R is the expression of a local difference between the R string and a patient sample variant calling sequence string P. As proposed in [Cleary2015], this local difference can be represented as a triple (a,s,e) where a is the alternative allele sequence issued from P, s is the inclusive start coordinate of the allele on R and e is the exclusive end coordinate. The reference allele is thus implicitly defined as $R_{s \ldots (e-1)}$. The variant annotation module 223 may be adapted to automatically process this triplet variant representation, so that the parameters of a variant v=(a,s,e) may be obtained by the following accessor functions: alt(v)= a, start(v)=s and end(v)=e.

As will be apparent to those skilled in the art of computer science, other representations are also possible, for instance with e' as the inclusive end coordinate instead of e and the reference allele implicitly defined as $R_{s \ldots e'}$. Another common notation that emphasizes the sequence string change for a variant is s:r>a where r is the reference allele and a is the alternative allele sequence issued from the patient sample variant calling sequence string P.

As will be apparent to those skilled in the art of bioinformatics, the reference sequence identifier, such as the chromosome or protein sequence name, may be implicit in this exemplary embodiment representation, under the assumption all patient variants to be compared are defined on the same reference sequence and using the same coordinate system. If different coordinate systems and/or different reference sequences need to be used, it may be possible to pre-process them to align them to one or another reference prior to identifying the matching variants. Let $V^*=\{v_2^*, \ldots, v_{|V|}\}$ denote a set of patient variants on R that were obtained from a given patient sample, sorted by the variants start coordinates. Let $D=\{d_1, d_2, \ldots, d_{|D|}\}$ be the set, also defined on the reference sequence R, of independent variants in the medical reference variant database that are to be assessed against V. In a possible embodiment, D may be a subset of the reference variants that are at a distance of at most z symbols from any patient variant $v_i^*$ in $V^*$, where z is a horizon parameter that determines the maximum coordinate distance at which a match possibly involving different variant representations could still be possible within the overall genomic region to be analyzed for the patient. As will be apparent to those skilled in genomics, the value of the horizon parameter z may be selected by the variant annotation module 223 depending on several parameters, among which the maximum distance an indel could be shifted to an alternate equivalent alignment, the maximum length of the complex variants, the read length, or a combination thereof. In a possible embodiment, with the current NGS sequencer technologies and when using the simple nucleotide symbol representation and coordinate system, this parameter may also be predefined as a length of 500 nucleotide symbols, but other values in this or other representation coordinate systems are also possible, for instance a horizon length of 100 symbols, 200 symbols, 300 symbols, 400 symbols, 600 symbols, 700 symbols, 800 symbols, 900 symbols, 1000 symbols, 1500 symbols, etc.

As will be apparent to those skilled in the art of bioinformatics, databases variants that are defined on another reference sequence or that are beyond the horizon z are then de facto excluded from the search as they cannot match any variant in V*. In a possible embodiment, the subset of reference variants D within the search horizon may be obtained by a coordinate-based retrieving from the reference databases, using an index-based search such as the tabix index for instance.

The problem to be solved then consists in assessing each database entry $d \in D$ as a possible match in V. In a possible embodiment, as a further heuristic to improve the computational efficiency of the search around the variant database entry d, a local horizon parameter $z_d$ may be used to select the subset $V \subseteq V^*$ within the maximum coordinate distance at which a match to the database variant entry d could still be possible, such as $V=\{v_j^* \in V^* \| pos(v_j^*) - pos(d) \| \leq z_d\}$, where pos( ) may be any of a start s( ) or an end e( ) coordinate. This subset thus includes the variants that can potentially match d. The remaining ones are beyond the local genomic region horizon $z_d$ around d and can therefore be excluded from the search. As will be apparent to those skilled in genomics, the value of the horizon parameter $z_d$ may be selected by the variant annotation module 223 depending on several parameters, among which the maximum distance a INDEL could be shifted to an alternate equivalent alignment, the maximum length of the complex variants, the read length, or a combination thereof. In a possible embodiment, with the current NGS sequencer technologies and when using the simple nucleotide symbol representation and coordinate system, this parameter may also be predefined as a length of 500 nucleotide symbols, but other values in this or other symbol representation and coordinate systems are also possible, for instance a horizon length of 100 symbols, 200 symbols, 300 symbols, 400 symbols, 600 symbols, 700 symbols, 800 symbols, 900 symbols, 1000 symbols, 1500 symbols, etc.

In a preferred embodiment, the variant annotation module 223 may then be adapted to identify whether the patient sample haplotype carries the variant database entry d. To this end, the variant annotation module 223 may implement the haplotype replay function h of [Cleary2015], which reconstructs larger haplotype strings by merging variants. For any sorted subsets $X=\{x_1, x_2, \ldots, x_{|x|}\} \subseteq V$, and provided that the start and/or the end coordinates s,e of any two variants $x_i$, $x_{i+1}$ do not overlap the same coordinate range, this function builds the haplotype string of X by concatenating alternatively the variant allele strings and the reference substrings from R. Following Cleary's formulation, the haplotype string of the patient variant subset X may be reconstructed as:

$$h(X)=h(X, k)+R_{e(x_x) \ldots (m+1)}$$

where+ represents the concatenation operation on string symbols, $h(X, 0)=\epsilon$, $\epsilon$ denotes the empty string, and for k>0

$$h(X, k)=h(X, k-1)+R_{e(x_{k-1}) \ldots s(x_k)-1}+a(x_k)$$

The variant annotation module 223 may thus be adapted to identify 345 the match status of any database entry d by looking for the subsets $X=\{x_1, x_2, \ldots, x_{|x|}\} \subseteq V$ such that:

$$S=\{X \subseteq V \| comp(h_{a \ldots b}(X), h_{a \ldots b}(d))=1\}$$

where $h_{a \ldots b}(X)$ is the haplotype obtained by replaying the patient sample variants in X into $R_{a \ldots b}$, and the coordinate boundaries a and b are defined such that they at least include the compared patient variants X and the database entry d. More formally: $a \leq min(s(v_1), s(d))$ and $b \geq max(e(v_{|v|}), e(d))$, and comp is a string comparison function that returns 1 if $h_{a \ldots b}(X)$ agrees with $h_{a \ldots b}(d)$, and 0 elsewhere. Note that this comp function is different from the indicator function $1_{h(X)h(y)}$ defined in [Cleary2015], which returns 1 if and only if h(X)=h(d), thus only identifying exact matches. In contrast, the proposed comp($h_1$, $h_2$) comparison function used for database searching may be designed to further account for included matches and not just exact matches, by tolerating symbol mismatches at specific locations between the replayed haplotype strings h1 and h2, as will now be described in further detail.

In a preferred embodiment, and provided that the lengths of the reconstructed haplotypes are the same |h1|=|h2|, the variant annotation module 223 may compare the symbols $h1_i$ and $h2_i$ for $1 \leq i \leq |h1|$ and mismatches may be tolerated according to the following rule: a haplotype string is made up of symbols issued from either the reference sequence or from the patient variant alternate sequence. The particular database haplotype string h(d) may accordingly be constructed by the proposed variant annotation module 223 as the concatenation of alt(d) the alternate sequence of the database entry with an extended region $RP_{left}=R_{a \ldots s(d)-1}$ on the left and/or $RP_{right}=R_{e(d) \ldots b}$ on the right part of alt(d) as:

$RP_{left}+alt(d)$, or $alt(d)+RP_{right}$, or more generally
$RP_{left}+alt(d)+RP_{right}$ The comp(h(X),h(d)) function may then tolerate mismatches between h(X) and h(d) provided three conditions are satisfied:

1) the length of the reconstructed haplotype strings from the patient sample variants equals the length of the reconstructed haplotype string from the variant database entry: $|h_{a \ldots b}(X)|=|h_{a \ldots b}(d)|$
and 2) the mismatch occurs either in the $RP_{left}$ or the $RP_{right}$ extended region part of the reconstructed database haplotype string h(d)
and 3) $e(x_1) \geq s(d)$ AND $s(x_{|x|}) \leq e(d)$, X being assumed sorted. If $x_1$ is an indel, then its right-most realignment coordinates are considered. If $x_{51 \ x|}$ is an indel, then the left-most realignment coordinates are considered. In plain words, all involved patient variant must overlap the location of the database variant.

FIG. 5 illustrates extended regions for medical reference variants database entries relative to a reference human genome sequence S=tattccgatcttagtcaaccag (FIG. 5a) respectively for:

a SNP variant entry 12:T>A, for which alt(d)=G (FIG. 5b)
an insertion variant entry 5:ε>CCGATGG, for which alt(d)=CCGATGG (FIG. 5c)
a deletion variant entry 10:CTTA>ε, for which alt(d) is an empty string (denoted by a triangle in FIG. 5d).

FIG. 6.1 illustrates an example of a complex patient variant v=10:CTTAG>AtAaC in which the SNP variant d=12:T>A is included and should be identified, annotated and reported even if there is no exact match between the patient variant replayed haplotype $h_{1 \ldots 20}(v)$ (FIG. 6b) and the database entry replay $h_{1 \ldots 20}(d)$ (mismatches in the left or right extended strings marked by the symbol for the sake of illustration in FIG. 6c).

FIG. 6.2 illustrates an example of a complex variant v=11:A>TC in which the insertion d=12:ε>C is included and should be identified, annotated and reported even if there is no exact match between the patient variant reconstructed haplotype $h_{1 \ldots 20}(v)$ (FIG. 6.2b) and the database entry replay $h_{1 \ldots 20}(d)$ (mismatches in the left or right extended strings marked by the '*' symbol for the sake of illustration in FIG. 6.2*c*). Note that due the the insertion, both the haplotype strings $h_{1 \ldots 20}$ are 21 symbols in length.

FIG. 6.3 illustrates an example of a set of two variants $X=\{x_1=14:GCC>TCG; x_2=20:CTT>\varepsilon\}$, consisting in a MNP and a deletion, and a database variant d=16: CATTC>GA, which is included and should be identified, annotated and reported even if there is no exact match between the patient two variants reconstructed haplotype $h_{1 \ldots 30}(X)$ and the database entry haplotype $h_{1 \ldots 30}(d)$ (FIG. 6.3*c*) (for the sake of illustration, mismatches in the left or right extended strings marked by the '*' symbol and the deletion location is indicated by a triangle). Note that due to the deletions, both the haplotype strings $h_{1 \ldots 30}$ are 27 symbols in length.

In order to efficiently detect the database variant entries matches, horizon parameters z and $z_d$ may be chosen so as to ensure that all matches, exact, included or composed will be detected within the extended replayed region. The horizon parameters may also be defined as a function of the length of the reads in the NGS sequencing workflow. The horizon parameters may also be pre-calculated as a function of the length of repeated nucleotide patterns in the genomic area to be analyzed by the genomic workflow, as these repetitions may affect the maximum distance at which equivalent representation, and particularly indels, may be shifted along the reference sequence. The horizon parameters may also be determined by the maximum length of the complex variants (MNPs and DELINS) that are analyzed.

Various further embodiments of the proposed identification method may also adapt the variant annotation module 223 to identify 345, annotate 346 and report 350 the exact as well as the included variant matches in at least one medical variant reference database so that the end user can more easily identify the haplotypes of medical relevance, regardless of the diversity of the genomic data analyzer workflow algorithms and reference data representation models. Various embodiments may also optimize the processing time of the proposed improved variant identification method in a genomic data analyzer workflow 220. Examples of such embodiments will now be described in more detail.

Using a Binary Tree to Optimize the Identification of the Combinations X in the Patient Variant Set V that Match D The solution space corresponds to all possible subsets $X \subseteq V$. A brute force approach would imply the exploration of $2^{|v|}$ combinations, which is computationally intractable in most practical applications of the human genome variant analysis for medical purposes. In a possible embodiment, the variant annotation module 223 may be further adapted to solve the problem in linear time with a branch-and-bound-like (B&B) algorithm. First, the database entry may be replayed into the reference genome by taking care that the resulting haplotype fully covers the same region as V:

$$h_{a \ldots b}(d)$$

This haplotype, shortly referred to as h(d), may be kept unchanged during the exploration process. In the example of FIG. 7*a*), the patient variant set comprises three simple variants:

$V_1$) 4:ε>GA (insertion)
$V_2$) 5:a>T (SNP)
$V_3$) 6:t>C (SNP)

while the medical reference variant database comprises a single complex entry:

DB) 6:t>GAC (DELINS)

The haplotype to be covered is thus h(6:t>GAC)=gaGAC.

The possible combinations of the patient variants however may be explored in a stepwise way by adding one variant at a time to the patient haplotype, and by comparing the extension to h(d). The exhaustive set of solutions can be represented by a haplotype binary tree as illustrated in the example of FIG. 7*b*), where each leaf represents a possible combination X, and an internal node at level k corresponding to a partial combination among the k first variants from X. Each level either corresponds to the rejection (for instance, left branch—corresponding to the reference allele) or to the confirmation (for instance, right branch—alternative allele) of a particular variant $v_i \in V$, defining thus the particular combination X. The branches are assessed bay string comparison against the replayed database entry haplotype. Sub-trees below the non-matching branches (represented with dashed lines) do not need to be further explored and can be discarded from the search. The path indicating the matching combination, by combining v1 and v3) is represented by bolded lines. FIG. 7*c*) shows an example extended replayed database entry haplotype with the matched alleles, either reference alleles (v2) or alternative alleles (v1, v3—represented by capital letters).

Each allele addition may then be assessed against h(d) using the proposed identification method with the comp function to identify both exact and included matches. If the comparison fails, then the underlying sub-tree does not need to be further constructed and can be discarded from the search. A path in the binary tree that successfully spells the reference or the alternate allele of each variant from the root until the last variant $v_{|v|}$ is then identified as a match of the medical reference variant database entry d.

Post-Processing Assessment of Composed Match According to Possible Variant Phasing Information The variant annotation module 223 may also further identify 345, annotate 346 and report 350 the patient variants which correspond to a haplotype of possible medical relevance by associating the individual variants according to their phasing information. This information provides variants relationships regarding the alleles on which they occur. Human germline samples display two alleles, one from each chromosome, while somatic samples may display more alleles. Variants occurring on the same allele are said in-phase, while the ones occurring on opposite alleles are said anti-phase. When no phase information can be obtained for some variants, the variants are said unphased.

When applied to database searching, phasing information does not affect the variant comparison procedure but can simply be used in a post-processing step by filtering the matches. Indeed, phasing enables to determine whether the variants are on the same chromosome, to determine the actual haplotype information and thus its functional genomics relevance. In particular, when the matches are composed (involving more than one individual variant), the variant annotation module 123 should primarily identify 345, annotate 346 and report 350 those compositions that are possible because they are on the same phase.

The phasing information enables to combine the patient variants into larger haplotypes. A haplotype may be reported 350 as confirmed if and only if all involved variants are in-phase. Combinations of variants that are anti-phase can be ignored in the post-processing phasing assembly because the resulting haplotype cannot exist in the real sample. If some phasing information is lacking so that it is not possible to discriminate between the in-phase and out-of-phase status of the variant composition, then the haplotype may be reported 350 as potential.

Alternative Reference Variant Representation Models

A simple representation model as represented for instance in the examples of FIG. 1, FIG. 4, FIG. 5, FIG. 6 and FIG. 7 consists in describing genomic variants with reference to the DNA sequence representation model, with the four DNA nucleotides respectively represented by the A, T, C and G symbols. However, the proposed methods may also work on other string representations of the genomic or proteomic information. Some medical reference databases of interest to diagnosis and personalized medicine treatment information may rather describe the variant at the protein level, such as the COSMIC database (Forbes et al., "*COSMIC: Somatic Cancer Genetics at High-Resolution*" in Nucleic Acids Research 45 (D1): D777-83, 2017-doi:10.1093/nar/gkw1121) that is dedicated to somatic mutations. Such mutations are found in tumor cells instead of being transmitted by the parents to their offspring, so they display more diversity in the affected population. In scientific publications, researchers often report such mutations at the protein level only. Indeed, by using the protein representation instead of the DNA one allows to account for all possible DNA mutations causing the described change at the protein level. Protein variants described in one patient can be matched to another patient even when the mutations at the DNA level are not exactly the same for the two patients. It is therefore a more useful representation to account for the significant diversity of possible DNA mutations in somatic cells.

Reference variant databases may also include extended symbols. Extended symbols are particularly useful in a particular database search application called hotspots screening. Hotspots screening analysis consists in analyzing a patient sample with regards to a predefined list of mutations that are called hotspots. The list of hotspots can be seen as a custom variant database against which the patient variants are matched. The referenced variant identification process 345 consists then in assessing the presence or the absence of each hotspot in the list. By restricting the test scope to the relevant mutations only, such analysis simplifies and reduces the time for the clinicians to get the relevant information that is related to some disease. As for database searching, hotspots screening requires a robust variant matching algorithm 345 to guarantee that all hotspots are correctly identified 345 by the variant annotation module 223. In practice, hotspots are commonly defined using an extended alphabet. Extended alphabet contains symbols that represent subsets of some symbols. For example, the extended DNA symbol "W" means both "A" and "T". Extended symbols provide a way to define a range of mutations using a single symbol. For this purpose, the comp(h1, h2) function can involve symbol comparison methods that account for extended symbols matching, allowing thus to identify the referenced variants that are described using such an extended alphabet.

Defining database entries (hotspots) using an extended alphabet is particularly useful for somatic analysis, were observed variants display more versatility. For example, a somatic variant often observed in the BRAF gene is V600E (valine at position 600 is replaced by glutamic acid). Though V600E is the most observed amino acid, other mutations at this position, V600K, V600M and V600D are observed as well. It is therefore useful to use an extended variant description format such as V600[EKMD] that match any of these amino acid mutations.

The proposed methods may also work with RNA sequences as a possible reference representation model, for instance with a RNA-seq next generation sequencing workflow. In general, the variant annotation module 223 operates with a proteomic representation on the translated cDNA sequence, but it may also apply the method directly on the RNA string representation, whose symbols are {AUGC).

Splitting the Whole Task into Independent Regions

In practical implementations, the reference sequence R may also be further split into independent non-overlapping regions based on the variants occurrence density, that is regions which are sufficiently far apart on the human genome to exclude any possible overlap of the sequencing reads in a next generation sequencing workflow. Those regions define partitions of the whole patient variants set so that each partition can be processed independently, to enable multitasking or distributing over a parallel computing architecture the variant annotation module 223 tasks for more efficient computational implementation of the genomic data analyzer workflow 220.

In a possible embodiment, the regions may be determined using horizon parameters $z$, $z_d$ that defines the minimal coordinate distance in the reference coordinate system above which two variants can be considered independent and thus do not need to be replayed into the same haplotype. The horizon parameters depend on the largest distance an insertion or a deletion could be shifted as well as on the sequencing reads length. In a possible embodiment, with the current NGS sequencer technologies and when using the simple nucleotide symbol representation and coordinate system, a typical value in is 500 nucleotides, but other values are also possible, for instance 100 nucleotides, 200 nucleotides, 300 nucleotides, 400 nucleotides, 600 nucleotides, 700 nucleotides, 800 nucleotides, 900 nucleotides, 1000 nucleotides, 1500 nucleotides, etc. Regions may be determined such that a coordinate distance of at most the horizon separates any two consecutive variants in a region. The partitioning procedure is trivial provided that the patient variants set is sorted according to the variants start coordinates.

Experimental Data

In one experiment, the proposed genomic data analyzer 220 has been embedded into the Sophia Genetics Data Driven Medicine (DDM) genomic analysis software workflow 220 and operated on a set of patient samples to identify variants of clinical relevance in the BRCA2 gene. Variant calling information is represented using the HGVS notation for cDNA coordinates and comprises complex MNP variants. The reference sequence is the transcript NM_000059 The medical reference variant database is Clinvar.

The proposed variant annotation module 223 identified 345, annotated 346 and reported 350 the pathogenic Clinvar deletion variant rs80358464 as an included match of a patient MNP mutation in the BRCA2 gene as an included match:

DB Clinvar: rs80358464: c.1800T>A

Patient        MNP        variant        :
    c.1799_1806ATAAAGGA>TATAAAGG wherein the star symbol '*' indicates the position of a matched nucleotide.

The proposed variant annotation module 223 also identified 345, annotated 346 and reported 350 the pathogenic Clinvar deletion variant rs80359642 as an included match of a patient DELINS mutation in the BRCA2 gene as an included match:

DB Clinvar: rs80359642: c.7211_7212delAA

Patient DELINS variant : c.7209_7212CAAA>GG wherein the star symbol '*' indicates the position of a matched nucleotide.

In another experiment, the proposed genomic data analyzer 220 has been embedded into the Sophia Genetics Data Driven Medicine (DDM) genomic analysis software workflow 220 and operated on a patient sample to identify variants of clinical relevance in the ARSD gene. Variant calling information is represented using the genomic notation seqId:startCoord:ref: alt and comprises complex DELINS variants. The reference sequence is the transcript NM_001669 (https://www.ncbi.nlm.nih.gov/nuccore/nm_001669). The medical reference variant database is Cosmic. The proposed variant annotation module 223 identified 345, annotated 346 and reported 350 the pathogenic Cosmic DELINS variant COSM5421975 (http://cancer.sanger.ac.uk/cosmic/mutation/overview?id=5421975) as a composed confirmed match of three patient mutations comprising two SNPs and a deletion.

DB Cosmic: COSM5421975: X:2835993: "GGCAGCCCACGCCGG">"AGAAGC"

Patient variants :
    X:2835993:"G">"A"
    X:2835995:"C">"A"
    X:2835999:"CCACGCCGG">""

Other Embodiments and Applications

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

As will be apparent to those skilled in the art statistics, the methods described herein may be indifferently applied to various statistical methods such as probability representations and statistical measurements. The terms "distribution", "likelihood", "probability" may thus be used indifferently throughout this specification.

Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, units, or mechanisms. Modules or units may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method for identifying, with a variant annotation module on at least one data processor, if the variant calling information of a patient sample includes at least one variant entry in a plurality of medical variant reference databases, a variant v being defined by a start coordinate s(v), an end coordinate e(v) and a string alt(v) of a genomic variation relative to a human genome reference string R, characterized in that the method comprises:

acquiring the variant calling information of the next generation sequencing data of a patient biological sample via the variant calling module on a genomic data analyzer operative to compare the next generation sequencing data to a reference genome to retrieve the variant calling information, the variant calling information comprising a set V* of genomic variants in at least one genomic region to be analyzed;

retrieving, in the plurality of medical variant reference databases, a subset D={$d_1$, $d_2$, . . . ,$d_{|D|}$} of reference variant database entries defined on the human genome reference string R matched to at least one variant in the patient set of genomic variants V*, wherein retrieving D comprises the variant calling module querying the entries in the plurality of medical variant reference databases, wherein the variant annotation module, via the at least one data processor, sequentially searches the plurality of medical variant reference databases for all reference variant database entries;

selecting, for each reference variant database entry d∈D, a subset V={$v_1$, $v_2$, . . . , $v_{|V|}$}, V⊆V*, of patient variants defined on the human genome reference string R matched to the reference variant database entry d, wherein V⊆V* is selected via the variant annotation module;

selecting an extended genomic region coordinate range a . . . b, the start and end coordinate boundaries a and b being defined such that they at least include the start and end coordinates from all the patient variants in the subset V, as well as the start and end coordinate of the variant database entry d;

reconstructing, with the variant annotation module, over the extended genomic region coordinate range a . . . b, a database variant haplotype string $h_{a . . . b}$(d) for the reference variant database entry d as the concatenation of three genomic information strings $RP_{left}$+alt(d)+ $RP_{right}$, wherein alt(d) is the alternative string characterizing the variant d, $RP_{left}$ is a string corresponding to extended genomic region on the left of the variant alt(d) in the reference human genome R and $RP_{right}$ is a string corresponding to extended genomic region on the right of the variant alt(d) in the reference human genome R;

reconstructing, with the variant annotation module, over the extended genomic region coordinate range a . . . b the patient variant haplotype string $h_{a . . . b}$(X), X being a subset of the selected region variant calling information V comprising at least one selected patient variant $v_j$;

identifying, with the variant calling module, that the variant calling information of the patient sample includes the medical variant database entry d if the length of the reconstructed database variant haplotype string $h_{a . . . b}$(d) equals the length of the reconstructed patient variant haplotype string $h_{a . . . b}$(X), the reconstructed patient variant haplotype string $h_{a . . . b}$(X) differs from the reconstructed database variant haplotype string $h_{a . . . b}$(d) by at least one mismatch in either the $RP_{left}$ string or the $RP_{right}$ string of the reconstructed database variant haplotype string $h_{a . . . b}$(d), and every variants in the subset X of patient sample variants overlaps by at least one symbol with the location defined by the start and the end coordinates of the database variant entry d.

2. The method of claim 1, wherein the extended region string $RP_{left}$ on the left of the variant alt(d) is an empty string and the extended region string $RP_{right}$ on the right of the variant alt(d) is at least one symbol long.

3. The method of claim 1, wherein the extended region string $RP_{right}$ on the right of the variant alt(d) is an empty string and the extended region string $RP_{left}$ on the left of the variant alt(d) is at least one symbol long.

4. The method of claim 1, wherein retrieving the subset D of database variant entries that may be matched to at least one variant in the patient set of genomic variants V* further comprises:

retrieving a database variant entry for the subset D if the start or the end coordinate of the database variant entry is within a distance of at most a horizon parameter z of symbols beyond the start or the end coordinate of any variant in the patient set.

5. The method of claim 4, wherein the horizon parameter z is predefined as a length of 500 symbols, 100 symbols, 200 symbols, 300 symbols, 400 symbols, 600 symbols, 700 symbols, 800 symbols, 900 symbols, 1000 symbols, or 1500 symbols.

6. The method of claim 4, wherein the horizon parameter z is calculated as a function of the maximum distance an INDEL could be shifted into an alternate equivalent alignment, of the maximum length of the genomic variants, of the read length, or of a combination thereof.

7. The method of claim 1, wherein selecting, for each variant database entry $d \in D$, the subset V of patient variants that may be matched to the variant database entry d further comprises:

selecting a patient variant $v_j$ from the set V* if the start or the end coordinate of the patient variant entry $v_j$ is within a distance of at most a local horizon parameter $z_d$ symbols beyond the start or the end coordinate of the variant database entry d.

8. The method of claim 7, wherein the local horizon parameter $z_d$ is predefined as a length of 500 symbols, 100 symbols, 200 symbols, 300 symbols, 400 symbols, 600 symbols, 700 symbols, 800 symbols, 900 symbols, 1000 symbols, or 1500 symbols.

9. The method of claim 7, wherein the local horizon parameter $z_d$ is calculated as a function of the maximum distance an INDEL could be shifted into an alternate equivalent alignment, of the maximum ref or alt length of the genomic variants, of the read length, or of a combination thereof.

10. The method of claim 1, wherein the genomic information strings are represented in a DNA nucleotide reference alphabet and coordinate system.

11. The method of claim 1, wherein the genomic information strings are represented in a cDNA reference alphabet and coordinate system.

12. The method of claim 1, wherein the genomic information strings are represented in a protein reference alphabet and coordinate system.

13. The method of claim 1, wherein the genomic information strings are represented in genomic hotspots extended alphabet and coordinate system.

14. The method of claim 1, herein the genomic information strings are represented in an RNA reference alphabet and coordinate system.

15. The method of claim 1, wherein all possible haplotypes obtained by the combinations $X \subseteq V$ of patient variants are represented into a binary tree, where each path from the root to the leaf represents a possible combination X, an internal node at level k corresponds to a partial combination involving k first variants from X, and the binary branches at each level k either correspond to the rejection or to the confirmation of a particular variant $v_i \in V$ in the possible combination X.

16. The method of claim 15, wherein reconstructing the patient variant haplotype string $h_{a \ldots b}(X)$ comprises:

constructing the branches in the binary tree that are either exactly matching ($h_{a \ldots b}(X) = h_{a \ldots b}(d)$) or including the reconstructed database entry haplotype string $h_{a \ldots b}(d)$, and aborting the construction of the sub-trees below the non-matching branches.

17. The method of claim 1, further comprising comparing the phasing information for the patient variants in the subset X, the subset X comprising at least two patient variants, and identifying the patient haplotype composed of the at least two variants as confirmed if and only if all involved variants are in-phase.

\* \* \* \* \*